United States Patent [19]

Kahn

[11] Patent Number: 5,446,128
[45] Date of Patent: Aug. 29, 1995

[54] ALPHA-HELIX MIMETICS AND METHODS RELATING THERETO

[75] Inventor: Michael Kahn, Bellevue, Wash.

[73] Assignee: The Board of Trustees of the University of Illinois, Urbana, Ill.

[21] Appl. No.: 236,240

[22] Filed: May 2, 1994

Related U.S. Application Data

[63] Continuation of Ser. No. 79,316, Jun. 18, 1993, abandoned.

[51] Int. Cl.$^6$ .................. A61K 38/00; C07K 5/00; C07K 7/00; C07K 17/00
[52] U.S. Cl. .................................. 530/317; 530/300; 530/324; 530/330
[58] Field of Search ................ 530/317, 300, 324, 330

[56] References Cited

PUBLICATIONS

Hruby et al., Biochem. J., vol. 268, pp. 249–262 (1990).

*Primary Examiner*—Jill Warden
*Assistant Examiner*—Sheela J. Huff
*Attorney, Agent, or Firm*—Seed and Berry

[57] ABSTRACT

There are disclosed alpha-helix mimetics and methods relating to the same for imparting or stabilizing alpha-helicity to a peptide or protein. In one aspect, the alpha-helix mimetics contain six- or seven-membered rings covalently attached at the end or within the length of the peptide or protein. The alpha-helix mimetics render the resulting peptide or protein more stable with regard to thermal stability, as well as making the peptide or protein more resistant to proteolytic degradation. In addition, the alpha-helix mimetics may be used in standard peptide synthesis protocols.

8 Claims, 4 Drawing Sheets

ALPHA-HELIX MIMETICS AND METHODS RELATING THERETO

STATEMENT OF GOVERNMENT INTEREST

This invention was made with government support under Grant No. GM-38260 awarded by the National Institute of Health, and Grant No. CHE-8657046 awarded by the National Science Foundation. The government may have certain rights in this invention.

CROSS-REFERENCE TO RELATED APPLICATION

This application is a continuation of U.S. application Ser. No. 08/079,316 filed Jun. 18, 1993, now abandoned.

TECHNICAL FIELD

This invention relates generally to alpha-helix mimetics and, more specifically, to alpha-helix mimetics which stabilize the alpha-helical structure of a natural or synthetic peptide or protein.

BACKGROUND OF THE INVENTION

Proteins are polymers of amino acids in which the carbon atoms and amide groups alternate to form a linear polypeptide, and with the amino acid side chains projecting from the α-carbon atom of each amino acid. The sequence of amino acids and location of disulfide bridges (if any) are considered the "primary" protein structure. The "secondary" structure of a protein refers to the steric relationship of amino acid residues that are in close proximity to one another in the linear sequence. Such steric relationships give rise to periodic structure, including the alpha-helix.

The alpha-helix is a rod-like structure wherein the polypeptide chain forms the inner part of the rod, and the side chains extend outward in a helical array. The alpha-helix is stabilized by hydrogen bonds between the NH and CO groups of the polypeptide chain. More specifically, the hydrogen of the NH group of each amino acid (i.e., amino acid residue "n") is hydrogen bonded to the oxygen of the CO group that is located four amino acid residues behind in the linear polypeptide (i.e., amino acid residue "n-4"). Such hydrogen bonding is illustrated below:

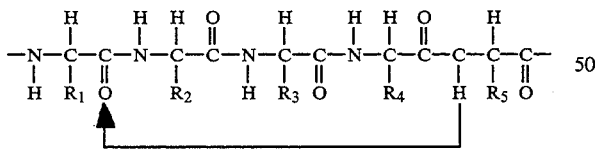

While only a single hydrogen bond is depicted above for purpose of illustration, each of the CO and NH groups of the linear polypeptide are hydrogen bonded in the alpha-helix. In particular, each amino acid is related to the next by a translation of 1.5 Å along the helix axis and a rotation of 100°, which gives 3.6 amino acid residues per turn of the alpha-helix. The pitch of the alpha-helix is 5.4 Å (the product of the translation, 1.5 Å, and the number of residues per turn, 3.6), and the diameter of the alpha-helix is 2.3 Å. The "screw sense" of the alpha-helix can be right-handed (clockwise) or left-handed (counter-clockwise). While a few left-handed alpha-helixes do exist, most alpha-helixes found in naturally occurring proteins are right-handed.

In the absence of interactions other than hydrogen-bonding, the alpha-helix is the preferred form of the polypeptide chain since, in this structure, all amino acids are in identical orientation and each forms the same hydrogen bonds. Thus, polyalanine (i.e., [—NHCH(CH$_3$)CO—]n) exists as an alpha-helix. However, the presence of other amino acids within the polypeptide chain may cause instability to the alpha-helix. In other words, the amino acid side chains do not participate in forming the alpha-helix, and may hinder or even prevent alpha-helix formation. A striking example of such side chain dependency on alpha-helix formation is polylysine (i.e., [—NHCH((CH$_2$)$_4$NH$_2$)CO—]n). At a pH below 10, the NH$_2$ moiety in the side chain of lysine is charged (i.e., NH$_3^+$), and electrostatic repulsion totally destroys the alpha-helix structure. Conversely, at a pH above 10, the alpha-helix structure is preferred.

The alpha-helix constitutes one of the principle architectural features of peptides and proteins, and are important structural elements in a number of biological recognition events, including ligand-receptor interactions, protein-DNA interactions, protein-RNA interactions, and protein-membrane interactions. In view of the important biological role played by the alpha-helix, there is a need in the art for compounds which can stabilize the intrinsic alpha-helix structure. There is also a need in the art for methods of making stable alpha-helix structures, as well as the use of such stabilized structures to effect or modify biological recognition events which involve alpha-helical structures. The present invention fulfills these needs and provides further related advantages.

SUMMARY OF INVENTION

Briefly stated, the present invention is directed to alpha-helix mimetics and, more specifically to alpha-helix mimetics which stabilize the alpha-helical structure of a natural or synthetic peptide or protein.

In one aspect of this invention, alpha-helix mimetics are disclosed having the following structures I and II:

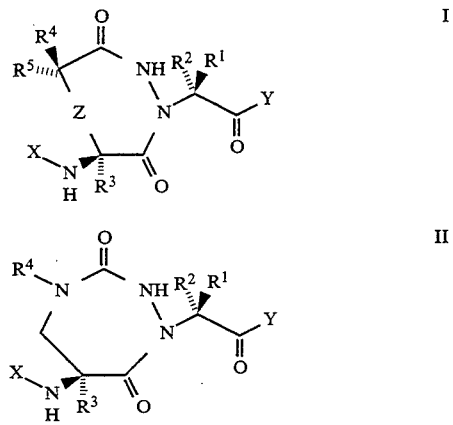

wherein Z is an optional methylene moiety (i.e., —CH$_2$—); R$^1$–R$^5$ are each selected from amino acid side chain moieties or derivatives thereof; and X and Y represent the remainder of the molecule. Amino acid side chain moieties include, but are not limited to, the amino acid side chains of glycine, alanine, valine, leucine, isoleucine, lysine, arginine, histidine, aspartic acid, glutamic acid, asparagine, glutamine, phenylalanine, tyrosine, tryptophan, cysteine, methionine, serine and threonine. Derivatives of amino acid side chain moieties include, but are not limited to, straight chain or branched, cyclic or noncyclic, substituted or unsubstituted, saturated or unsaturated lower chain alkyl and lower chain aryl moieties.

In another aspect, an alpha-helix modified peptide or protein is disclosed wherein an alpha-helix mimetic of this invention is covalently attached to at least one amino acid of a peptide or protein. In this embodiment, X and/or Y in the above structures I and II represent one or more amino acids of the peptide or protein. In still a further aspect, a method for imparting and/or stabilizing alpha-helicity of a peptide or protein is disclosed. This method includes covalently attaching one or more alpha-helix mimetics of this invention within, or to the end of, a peptide or protein.

Other aspects of this invention will become apparent upon reference to the attached figures and the following detailed description.

DETAILED DESCRIPTION OF THE INVENTION

Figure 1:
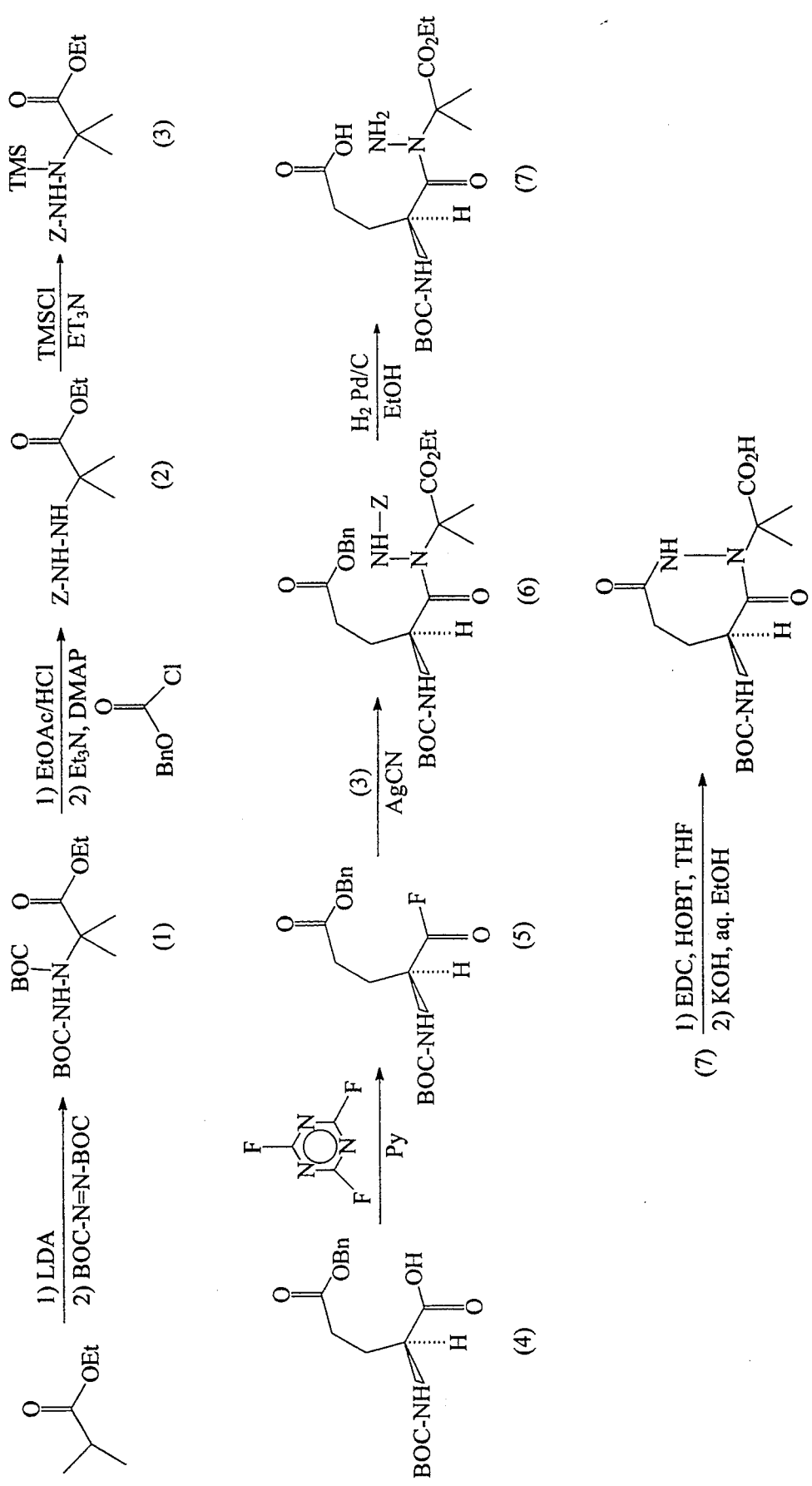
FIG. 1 is a schematic illustrating the synthesis of representative alpha-helix mimetics of this invention.

As mentioned above, the alpha-helix is an important structural component for many biological recognition events. The alpha-helix mimetics of this invention serve to impart and/or stabilize the alpha-helical structure of a natural or synthetic peptide or protein, particularly with regard to thermal stability. In addition, the alpha-helix mimetics of this invention are more resistant to proteolytic breakdown, thus rendering a peptide or protein containing the same more resistant to degradation.

The alpha-helix mimetics of this invention have the following structures I and II:

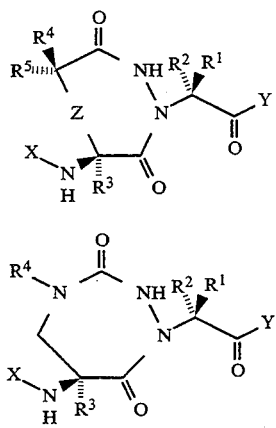

wherein Z (structure I) is an optional methylene moiety (i.e., —CH$_2$—); R$^1$–R$^5$ (structure I) and R$^1$–R$^4$ (structure II) are each selected from amino acid side chain moieties or derivatives thereof; and X and Y represent the remainder of the molecule. Although structures I and II have been depicted as preferred embodiments for right-handed alpha-helices, one skilled in the art will recognize that the mirror images of structures I and II would be used in left-handed alpha-helices.

When the optional methylene moiety Z is present in structure I, the alpha-helix mimetic is a seven-membered ring having the following structure III:

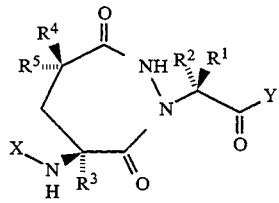

wherein R$^1$–R$^5$ are each selected from amino acid side chain moieties or derivatives thereof; and X and Y represent the remainder of the molecule. On the other hand, when the optional methylene moiety Z of structure I is not present, the alpha-helix mimetic is a six-membered ring having the following structure IV:

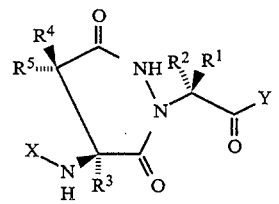

wherein R$^1$–R$^5$ are each selected from amino acid side chain moieties or derivatives thereof; and X and Y represent the remainder of the molecule.

The term "remainder of the molecule", as represented by X and Y in the above structures, may be any chemical moiety. For example, when the alpha-helix mimetic is located within the length of a peptide or protein, X and Y may represent amino acids of the peptide or protein. Alternatively, if two or more alpha-helix mimetics are linked, the Y moiety of a first alpha-helix mimetic may represent a second alpha-helix mimetic while, conversely, the X moiety of the second alpha-helix mimetic represents the first alpha-helix mimetic. When the alpha-helix mimetic is located at the end of a peptide or protein, or when the alpha-helix mimetic is not associated with a peptide or protein, X and/or Y may represent a suitable terminating moiety. Such terminating moieties include, but are not limited to, —H, —OH, —OR, —NH$_2$, —CHO, —NHR and —COR (where R is a lower chain alkyl or aryl moiety), as well as suitable peptide synthesis protecting groups (such as BOC and FMOC).

As used herein, the term "an amino acid side chain moiety" represents any amino acid side chain moiety present in naturally occurring proteins, including (but not limited to) the naturally occurring amino acid side chain moieties identified in Table 1.

TABLE 1

| Amino Acid Side Chain Moiety | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3$$^+$ | Lysine |
| —(CH$_2$)$_3$NHC(NH$_2$)NH$_2$$^+$ | Arginie |

TABLE 1-continued

| Amino Acid Side Chain Moiety | Amino Acid |
| --- | --- |
| —CH₂— (imidazole, HN, N) | Histidine |
| —CH₂COO⁻ | Aspartic acid |
| —CH₂CH₂COO⁻ | Glutamic acid |
| —CH₂CONH₂ | Asparagine |
| —CH₂CH₂CONH₂ | GLutamine |
| —CH₂—(phenyl) | Phenylalanine |
| —CH₂—(phenyl)—OH | Tyrosine |
| —CH₂—(indole) | Tryptophan |
| —CH₂SH | Cysteine |
| —CH₂CH₂SCH₃ | Methionine |
| —CH₂OH | Serine |
| —CH(OH)CH₃ | Threonine |

Other naturally occurring side chain moieties of this invention include (but are not limited to) the side chain moieties of 3,5-dibromotyrosine, 3,5-diiodotyrosine, hydroxylysine, γ-carboxyglutamate, phosphotyrosine, phosphoserine and glycosylated amino acids such as glycosylated serine and threonine.

In addition to naturally occurring amino acid side chain moieties, the amino acid side chain moieties of the present invention also include various derivatives thereof. As used herein, a "derivative" of an amino acid side chain moiety includes all modifications and/or variations to naturally occurring amino acid side chain moieties. For example, the amino acid side chain moieties of alanine, valine, leucine, isoleucine and phenylalanine may generally be classified as lower chain alkyl or aryl moieties. Derivatives of amino acid side chain moieties include other straight chain or branched, cyclic or noncyclic, substituted or unsubstituted, saturated or unsaturated lower chain alkyl or aryl moieties. As used herein, "lower chain alkyl moieties" may contain from 1-12 carbon atoms, and "lower chain aryl moieties" may contain from 6-12 carbon atoms. Substituted derivatives of lower chain alkyl or aryl moieties of this invention include (but are not limited to) one or more of the following chemical moieties: —OH, —OR, —COOH, —COOR, —CONH₂, —NH₂, —NHR, —NRR, —SH, —SR and halogen (including F, Cl, Br and I), wherein R is a lower chain alkyl or aryl moiety. Moreover, cyclic lower chain alkyl and aryl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole.

As mentioned above, the alpha-helix mimetics of this invention serve to impart and/or stabilize the alpha-helicity of a protein or peptide. The alpha-helix mimetic may be positioned at either the C-terminus or N-terminus of the protein or peptide, or it may be located within the protein or peptide itself. In addition, more than one alpha-helix mimetic of the present invention may be incorporated in a protein or peptide.

The alpha-helix mimetics of this invention have broad utility in a variety of naturally occurring or synthetic peptides and proteins. For example, neuropeptide Y ("NPY"), a polypeptide amide of 36 amino acids, is a potent vasoconstrictor and neuromodulator, and antagonists to NPY have anti-hypertensive activity. C-terminal analogs of NPY have previously been constructed, including the following analogs: Ac—RAAANLITR-QRY—NH₂ and Ac—RAAANAAARQRY—NH₂ (Ac represents that the amino-terminus is acetylated, and —NH₂ indicates that the carbon-terminus is an amide). The biological activity of the above analogs, as evidenced by binding to the NPY binding site, has been correlated to its alpha-helicity (see, Jung et al., *Biopolymers* 31:613–19, 1991). By substituting one or more of the alpha-helix mimetics of this invention for select amino acids within an NPY analog polypeptide, the alpha-helicity of the NPY analog may be enhanced, thus increasing its binding affinity and improving its biological activity. Suitable assays for determining bioresponse and binding are known, including the Guinea Pig Atrial Contraction Assay (Panlabs Inc., Bothell, WA; see also, Giuliani et al., *Br. J. Pharmacol.* 98:407–412, 1989), Discoveryscreen ™ Neuropeptide Y Binding (Panlabs, Inc., Bothell, WA; see also, Walker et al., *Molec. Pharmacol.* 34:778–792; Saria et al., *Eur. J. Pharmacol.* 107:105–107, 1985), Rat Vas Deferens Relaxation (EFS) (Panlabs, Inc., Bothell, WA; see also, Wahlested et al., *Regulatory Peptide* 13:307–318, 1986; Martel et al., *J. Pharmacol. Exp. Ther.* 38:494–502, 1990)(which references are hereby incorporated by reference in their entirety).

For example, the following structure V may be made by substituting an alpha-helix mimetic of structure III above for the "AAA" sequence of the NPY analog Ac—RAAANLITRQRY—NH₂:

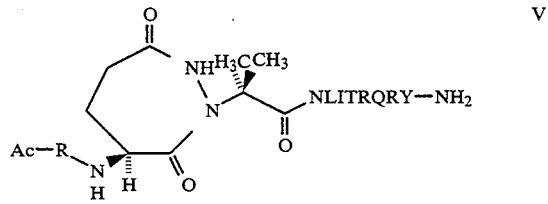

V

Similarly, the following structure VI may be made by substituting an alpha-helix mimetic of structure IV above for the "AAA" sequence of the NPY analog Ac—RAAANLITRQRY—NH₂:

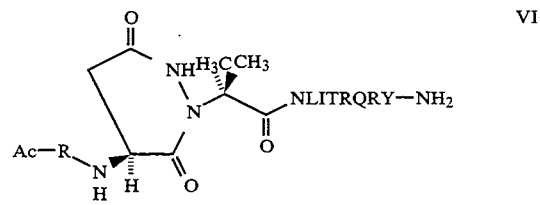

VI

Alternatively, more than one alpha-helix mimetic of the present invention may be utilized. For example, the following structure VII may be made by substituting two alpha-helix mimetics of structure III for the "AAA- NAAA" sequence of the NPY analog Ac—RAAA-NAAARQRY—NH2:

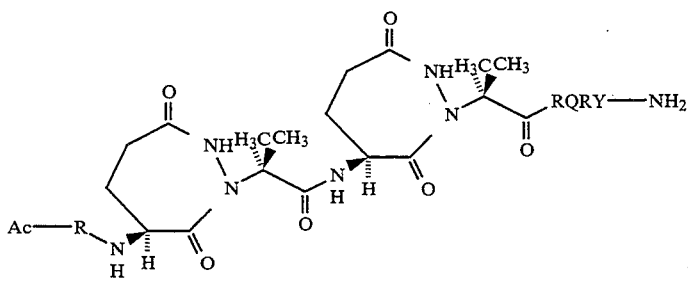

A further example of the utility of the alpha-helix mimetics of the present invention may be illustrated with regard to cytokines. Many cytokines (e.g., hGH, IL2 and IL4) are organized into a bundle of alpha-helical structures. In many instances the C-terminal alpha-helix is a critical site of interaction with its corresponding receptor. For example, C-terminal-stabilized alpha-helical peptides (stabilized with one or more of the alpha-helix mimetics of this invention) may serve as antagonists of IL2 and IL4, and have utility as anti-inflammatory agents. More specifically, the C-terminal of both IL2 and IL4 have been found critical in ligand-receptor interaction (see, Landgraf et al., JBC 264:816–22, 1989 and Ramanathan et al., Biochemistry 32:3549–56, 1993). The respective sequences for these regions are: (119)NRWITFCQSIISTLT(133) and (111)NFLERLKTIMREKYSPCSS(129). By synthesizing a peptide which contains one or more of the alpha-helix mimetics of this invention in place of certain amino acids in the above sequences, peptides can be made which will mimic the C-terminal of IL2 or IL4, thus serving as IL2 or IL4 receptor antagonists. For example, the following structures VIII, IX and X can be made by substituting one or more of the alpha-helix mimetics of structure III for select amino acids with the above IL2 C-terminal sequence:

(In structure VIII the cysteine residue of the IL2 C-terminal sequence has been replaced with alanine (i.e., C→A) since cysteine is prone to oxidation, and isoleucine has been changed to leucine (i.e., I→L) in structures VIII, IX and X to increase alpha-helicity.)

While the utility of the alpha-helix mimetics of this invention have been disclosed with regard to certain embodiments, it will be understood that a wide variety and type of compounds can be made which includes the alpha-helix mimetics of the present invention. For example, an alpha-helix of this invention may be substituted for two or more amino acids of a peptide or protein. In addition to improving and/or modifying the alpha-helicity of a peptide or protein, especially with regard to thermal stability, the alpha-helix mimetics of this invention also serve to inhibit proteolytic breakdown. This results in the added advantage of peptides or proteins which are less prone to proteolytic breakdown due to incorporation of the alpha-helix mimetics of this invention.

The alpha-helix mimetics of this invention may generally be synthesized by the condensation of a suitable derivative of a carboxylic acid XI or XII with a hydrazine moiety XIII:

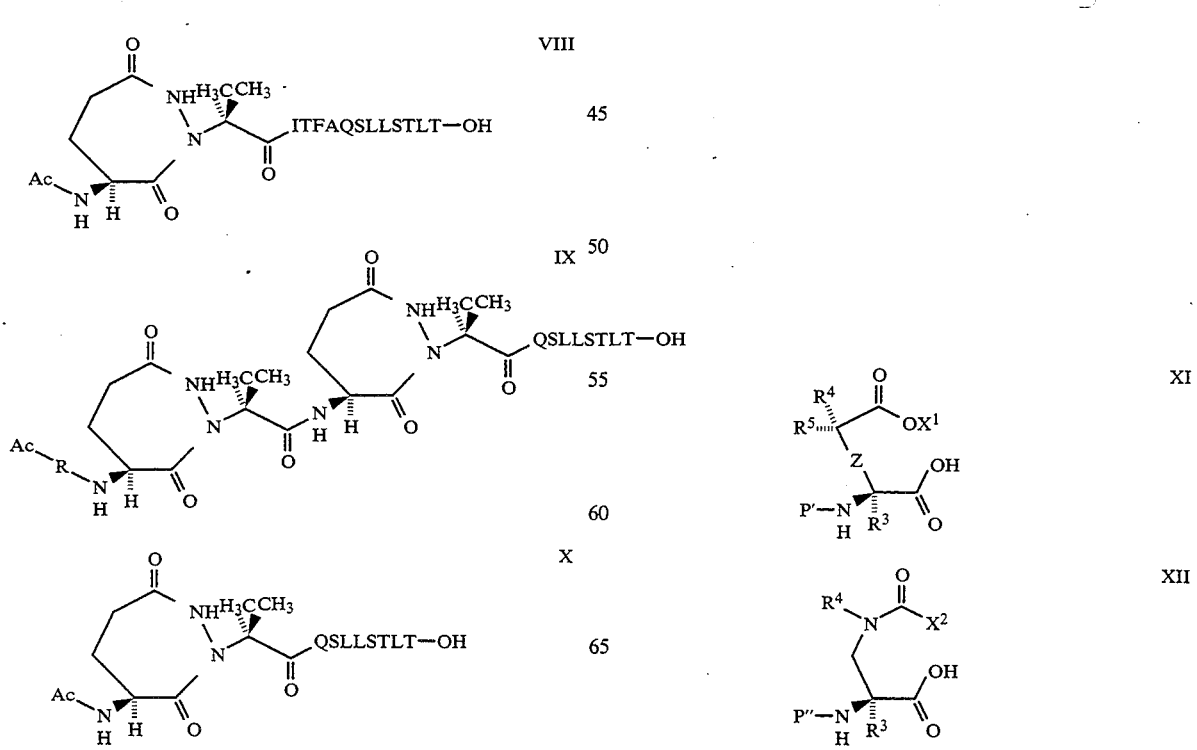

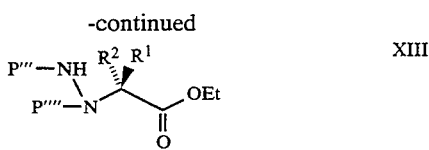

XIII wherein Z (structure XI) is an optional methylene moiety (i.e., —CH$_2$—); R$^3$–R$^5$ (structure XI), R$^3$–R$^4$ (structure XII) and R$^1$–R$^2$ (structure XIII) are each selected from amino acid side chain moieties or derivatives thereof; P'–P'''' are each selected from suitable peptide synthesis protecting groups, X$^1$ is a suitable carboxylic acid protecting group (such as methyl or benzyl), and X$^2$ is a suitable leaving group (such as chloride or imidazole). Following condensation of structures XI or XII with structure XIII, the resulting compound may then be cyclized to yield the corresponding structure I or II above. A more detailed disclosure with respect to synthesis of the alpha-helix mimetics of this invention is presented in the examples below.

The alpha-helix mimetics of the present invention may be used in standard peptide synthesis protocols, including automated solid phase peptide synthesis. Peptide synthesis is a stepwise process where a peptide is formed by elongation of the peptide chain through the stepwise addition of single amino acids. Amino acids are linked to the peptide chain through the formation of a peptide (amide) bond. The peptide link is formed by coupling the amino group of the peptide to the carboxylic acid group of the amino acid. The peptide is thus synthesized from the carboxyl terminus to the amino terminus. The individual steps of amino acid addition are repeated until a peptide (or protein) of desired length and amino acid sequence is synthesized.

To accomplish peptide (or protein) synthesis as described above, the amino group of the amino acid to be added to the peptide should not interfere with peptide bond formation between the amino acid and the peptide (i.e., the coupling of the amino acid's carboxyl group to the amino group of the peptide). To prevent such interference, the amino group of the amino acids used in peptide synthesis are protected with suitable protecting groups. Typical amino protecting groups include BOC and FMOC groups. Accordingly, in one embodiment of the present invention, the alpha-helix mimetics of the present invention bear a free carboxylic acid group and a protected amino group, and are thus suitable for incorporation into a peptide by standard synthetic techniques.

The following examples are offered by way of illustration, not limitation.

EXAMPLES

Example 1

Synthesis of Representative Alpha-Helix Mimetics of Structure I

A. Synthesis of Structure XIV:

This example illustrates the synthesis an alpha-helix mimetic having the following structure XIV:

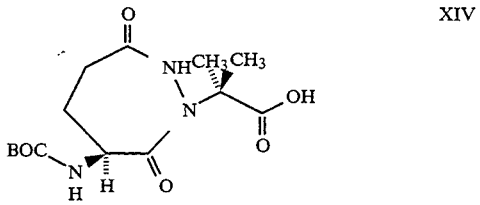

XIV

The following synthesis is presented schematically in FIG. 1. Synthesis of structure XIV was generally accomplished by condensation of hydrazine derivative (3) with carboxylic acid derivative (5). More specifically, protected hydrazine (3) was prepared in three steps from ethyl isobutyrate. First, the lithium enolate of the ethyl ester (generated by treatment with lithium diisopropylamide) was added to di-t-butyl azodicarboxylate to produce (after ammonium chloride quench) addition product (1) in 85 percent yield. The t-butyl carboxylate groups of (1) were removed by acid hydrolysis in ethyl acetate saturated with hydrochloric acid and the resulting hydrazine salt treated with benzylchloroformate, triethylamine, and dimethylaminopyridine in methylene chloride. N-benzylcarbamate (2) was thus produced in 59 percent yield. Protected hydrazine (3) was prepared in 99 percent yield by reaction of N-benzylcarbamate (2) with an excess of trimethylsilylchloride in triethylamine. Protected hydrazine (3) prepared as described was suitable for condensation.

A protected version of glutamic acid (4) (i.e., amino group t-butylcarbonate protected and side chain carboxylic acid benzyl protected) (Advanced Chemtech, Louisville, Ky.) was the starting material for the synthesis of the carboxylic acid. Specifically, carboxylic acid (4) was carboxy activated by conversion to the corresponding acid fluoride (5) by reaction with cyanuric fluoride and pyridine in methylene chloride. Acid fluoride (5) is a reactive intermediate and was not isolated but rather treated directly with protected hydrazine (3) and silver cyanide (2 equivalents) in benzene to produce diester (6) in 80% yield. Hydrogenolysis of (6) over 10 percent palladium on carbon in ethanol removed both benzyl and benzyl carbamoyl protecting groups to generate intermediate (7) which was self-condensed to the corresponding cyclic hydrazide in 52 percent yield by treatment with 1-(3-dimethylaminopropyl)-3-ethylcarbodiimide hydrochloride and 1-hydroxy-benzotriazole hydrate in aqueous tetrahydrofuran. Ester hydrolysis of the cyclic hydrazide with ethanolic potassium hydroxide gave alpha-helix mimetic XIV in 88 percent yield. The characteristics of the $^1$H-NMR spectrum of the methyl ester of structure XIV were as follows: BOC—NH (5.45δ, 1H, broad s), αCH (4.37δ, 1H, ddd, $J_1$=7Hz, $J_2$=5.7Hz, $J_3$=4.8 Hz), OCH$_3$ (3.72δ, 3H, s), —CH$_2$—CO—(2.78δ, 2H, m ), —CH$_2$—CH$_2$—CO—(1.85δ, 2H, m), BOC—NH (1.42δ, 9H, s), —C(CH$_3$)$_2$ (1.32δ, 6H, s). Similarly, the characteristics of the $^{13}$C—NMR spectrum of the methyl ester of structure XVI were as follows: —CO— (175 δ, 172δ, 171δ, 156.5δ), —NC(CH$_3$)$_2$CO— (82δ), —N—CH—CO— (62.5δ), —OCH$_3$ (53δ), —CH$_2$CO— (31.5δ), —CH$_2$CH$_2$CO— (29.0δ), —NC(CH$_3$)$_2$CO—(25.5δ, 24.0δ).

B. Synthesis of Structure XV:

This example illustrates the synthesis of an alpha-helix mimetic having the following structure XV:

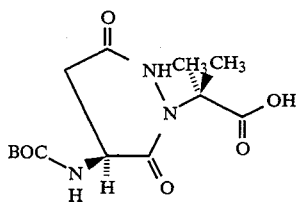

XV

The alpha-helix of structure XV is prepared in a synthetic reaction scheme identical to the scheme disclosed in FIG. 1 for structure XIV, except that instead of using a protected version of glutamic acid (i.e., compound (4) in FIG. 1) as a starting material, the following protected version of aspartic acid (4') was employed:

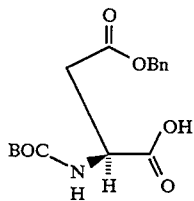

(4')

C. Synthesis of Other Alpha-Helix Mimetics

Other synthetic routes may be utilized to prepare alpha-helix mimetics of structure I. For example, to prepare derivatives of structure I where $R^3$ is methyl, α-methyl glutamic or aspartic acid may be utilized in a reaction sequence as illustrate in FIG. 1. These α-amethyl derivatives may be prepared as described in Zydowsky et al. (*J. Org. Chem.* 55:5437, 1990). In this reaction sequence, the methyl group is derived from reactant alanine. 2-hydroxybenzaldehyde is condensed with alanine under basic conditions to yield an intermediate which may be alkylated with either a 2-bromopropionic acid equivalent (or a 2-bromoethanoic acid equivalent) to yield, after hydrolysis, a α-methyl-glutaric (or aspartic) acid derivative suitable for condensation with a suitable hydrazine to provide the alpha-helix mimetic of structure I.

Alternatively, $R^4$ or $R^5$ substituted derivatives of structure I may be prepared as described in FIG. 1 utilizing 3-substituted glutamic or aspartic acid derivatives which may be prepared according to the procedure described in Baldwin et al. (*Tetrahedron* 45:1465, 1989). In this procedure, protected versions of these amino acids may be directly alkylated at the carbon alpha to the side chain carbonyl. Utilization of the resulting substituted derivatives in the reaction sequence described illustrated in FIG. 1 provides derivatives of structure I substituted at $R^4$ or $R^5$.

In addition to variations of the carboxylic acid derivatives utilized in the synthesis of alpha-helix mimetics of structure I, various substituted hydrazines may also be utilized. For example, hydrazine formation from acylcarbamates as described in Gennari et al. (*J. Amer. Chem. Soc.* 108:6394, 1986) may be utilized to provide substituted hydrazines which, when submitted to the reaction conditions described in FIG. 1, will provide derivatives of structure I with appropriate substitution variations at positions $R^1$ and $R^2$.

Example 2

Synthesis of Representative Alpha-Helix Mimetics of Structure II

This example illustrates the synthesis of an alpha-helix mimetic having the following structure XVI:

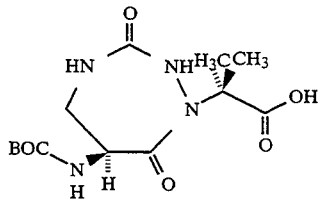

XVI

Figure 2A:
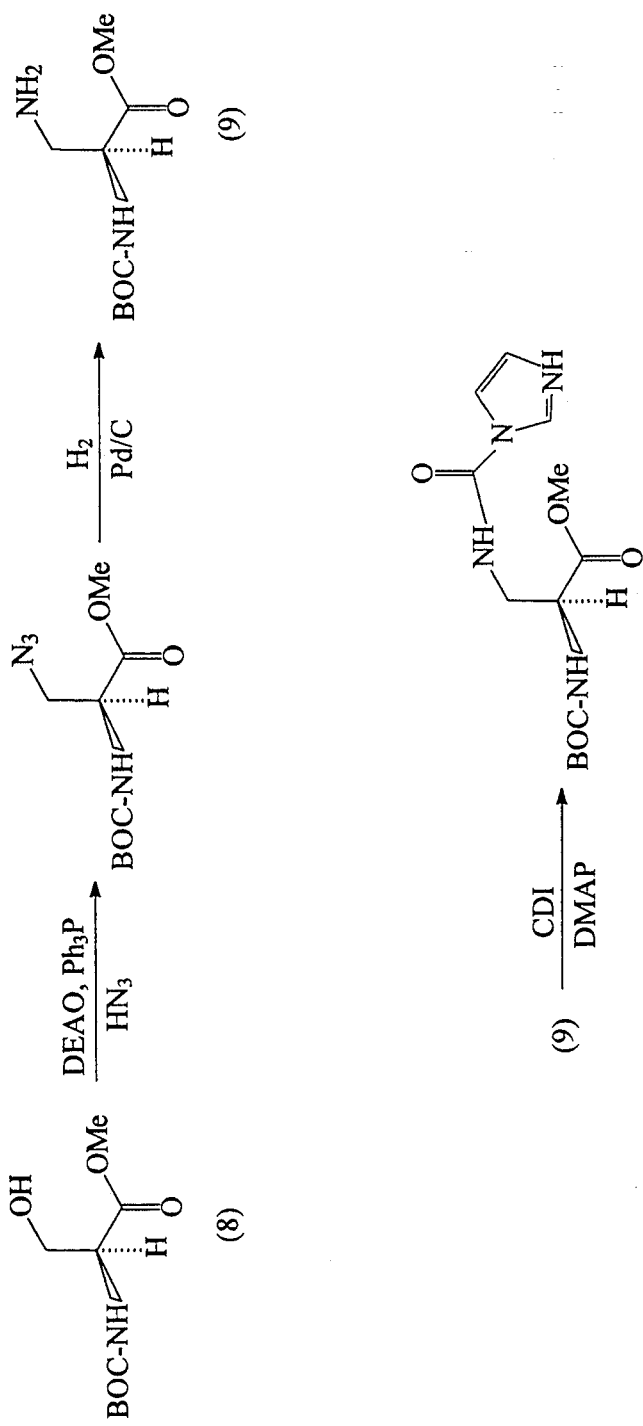
FIGS. 2(A), 2(B) and 2(C) are further schematics illustrating the synthesis of representative alpha-helix mimetics of this invention.
Figure 2B:
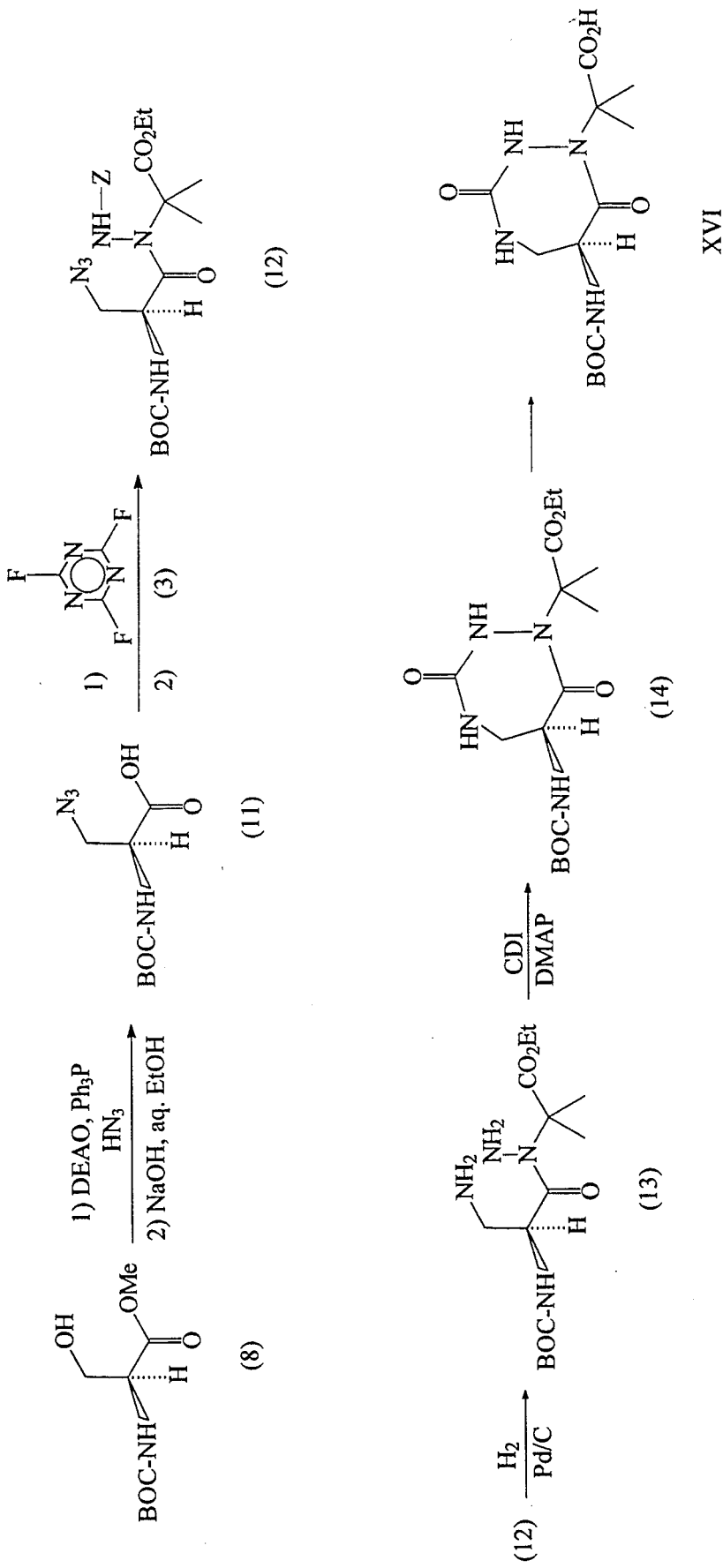

Synthesis of structure XVI may be accomplished by two methods. The first method is the two-step condensation of a protected hydrazine with a suitable derivative of a carboxylic acid as generally described in Example 1. In this method, the preparation of the carboxylic acid derivative is represented schematically in FIG. 2(A). The second method is represented in FIG. 2(B), and utilizes the protected hydrazine of Example 1.

A. Synthesis of Structure XVI:

To prepare an alpha-helix mimetic of structure XVI by the two-step condensation method of Example 1, a suitable derivative of carboxylic acid XII is first prepared. Referring to FIG. 2(A), such a derivative (wherein $R^3$ and $R^4$ are hydrogen and $X^2$ is imidazole) may be synthesized in three steps starting with a protected version of serine (8) (i.e., amino group t-butylcarbonate protected) (Advanced Chemtech, Louisville, Ky). Specifically, protected serine (8) is treated with diethyl azodicarboxylate, triphenylphosphine, and hydrogen azide to yield an intermediate serine azide derivative. Hydrogenolysis of the intermediate azide over palladium on carbon yields amine (9), a serine derivative where the side chain hydroxy has been substituted with an amino group. Alternatively, amine (9) may be prepared from aspartic acid via Curtius rearrangement. Treatment of amine (9) with carbonyl diimidazole produces carboxylic acid derivative (10) (i.e., structure XII where $R^3$ and $R^4$ are hydrogen, P" is BOC, and $X^2$ is imidazole). This carboxylic acid derivative is suitable for condensation with protected hydrazine (3) of FIG. 1 to yield structure XVI in a reaction sequence as described in Example 1.

B. Alternative Synthesis of Structure XVI:

Referring to FIG. 2(B), an alpha-helix mimetic having structure XVI may be prepared by cyclization of a suitable diamine. In this method, the seven-membered ring of the alpha-helix mimetic is formed in the last synthetic step by treating a suitable diamine with carbonyl diimidazole. The reaction sequence begins with a protected version of serine (8) (i.e., amino group t-butylcarbonate protected and carboxyl group methyl ester protected) (Advanced Chemtech, Louisville, Ky). As with the method illustrated in FIG. 2(A), the side chain hydroxyl of the serine methyl ester is first converted to an azide group with diethyl azodicarboxylate, triphenylphosphine, and hydrogen azide. The serine methyl ester is then hydrolyzed to the corresponding carboxylic acid (11) and then converted to its acid fluoride by treatment with cyanuric fluoride. The intermediate acid fluoride is then treated with protected hydrazine (3) of FIG. 1 to yield azide (12). Hydrogenolysis of

(12) over palladium on carbon reduces the azide group and removes the benzyl carbamoyl group to produce diamine (13). The seven-membered ring of the alpha-helix mimetic is formed by treatment of diamine (13) with carbonyl diimidazole and dimethylaminopyrridine, resulting in ethyl ester (14). Hydrolysis of (14) yields the alpha-helix mimetic of structure XVI.

Figure 2C:
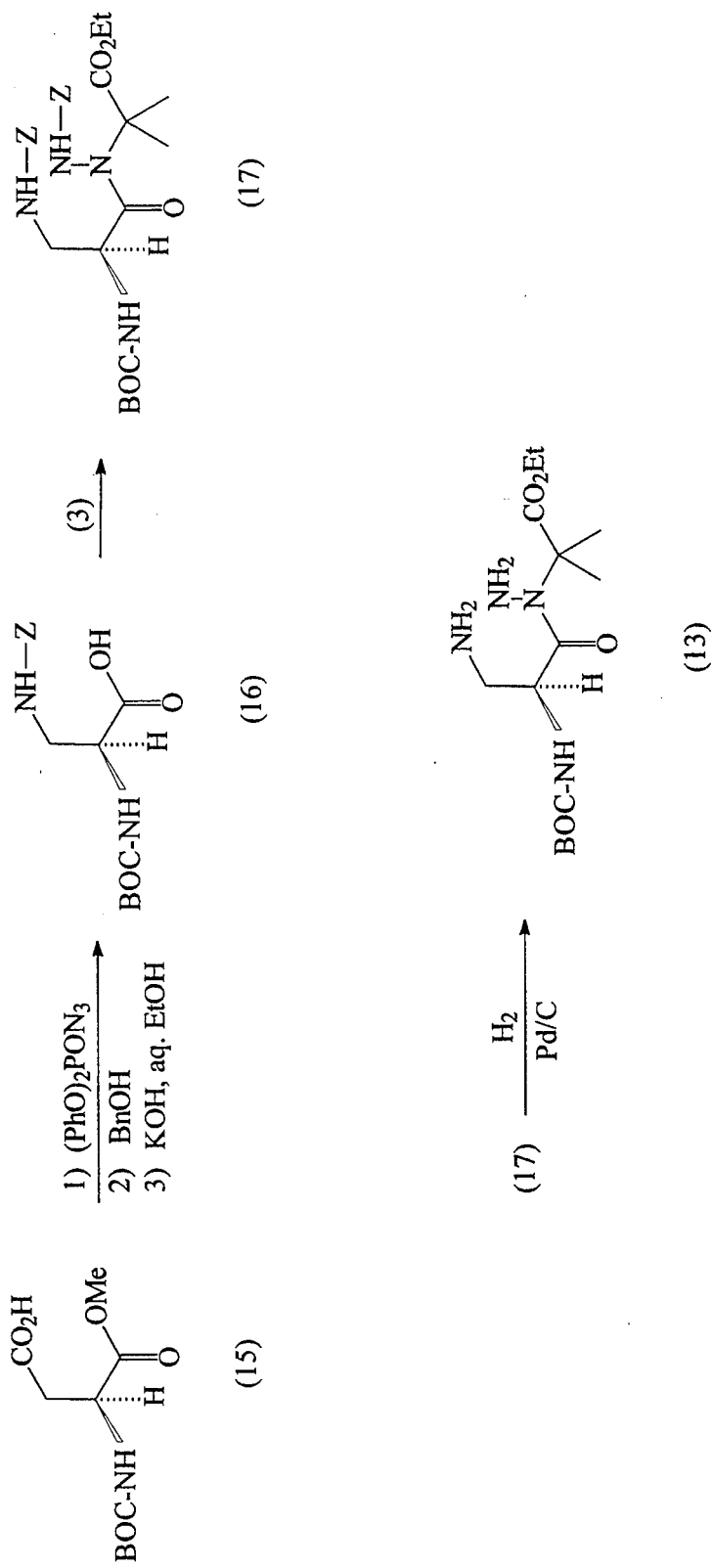

Alternatively, referring to FIG. 2(C), diamine (13) may be prepared from BOC-aspartic acid-α-methyl ester (15) via Curtius rearrangement. Treatment of (15) with diphenyl-phosphoryl azide, followed by reaction with benzyl alcohol, yields an intermediate benzyl carbamoyl ester which may be hydrolyzed to the corresponding carboxylic acid (16). Reaction of (16) with protected hydrazine (3) as shown in FIG. 2(B) produces protected diamine (17) which, upon hydrogenolysis, provides diamine (13).

Example 3

Synthesis of a Representative Peptide Containing an Alpha-Helix Mimetic

This example illustrates the synthesis of a peptide containing an alpha-helix mimetic of the present invention having structure VI.

Specifically, an alpha-helix mimetic having structure XV was synthesized according to the disclosure of Example 1, and incorporated into a peptide by standard solid phase peptide synthetic techniques to yield structure VI. The peptide of structure VI was synthesized on either PAM or MBHA (P-methyl benzhydrylamine) resin using an Advanced Chemtech ACT 90 model synthesizer. Couplings were conducted using 1-hydroxybenzotriazole, benzotriazolyl-oxy-tris-(dimethylamino) phosphonium hexafluorophosphate, and diisopropylethylamine in a mixture of dichloromethane and dimethylformamide at room temperature. Cleavage from the resin was accomplished with either hydrogen fluoride/anisole or ammonolysis. The resin was washed with ether and extracted with dilute acetic acid and evaporated to dryness in vacuo. The crude residue was purified by reverse phase C18 high performance liquid chromatography.

Example 4

Alpha-Helicity of a Representative Peptide Containing an Alpha-Helix Mimetic

This example illustrates the enhanced alpha-helicity of a peptide containing an alpha-helix mimetic of the present invention.

Alpha-helicity of a peptide is typically determined by measuring its circular dichroism (CD), and CD data is normally presented as mean residue ellipticies $[\Theta]_m$. Alpha-helical peptides show two negative Cotton effects at 208 nm and 222 nm, and a positive Cotton effect at 193 nm, while the CD spectra of peptides with random coil secondary structure are dominated by the increasing negative Cotton effect at shorter wavelength. Alpha-helicity may be estimated from the value at 222 nm, and by comparing the negative Cotton effects at 222 nm and 208 nm. Increasing fraction of $[\Theta]_m(222\ nm)$ divided by $[\Theta]_m(208\ nm)$ correlates with increasing alpha-helicity. High values for $[\Theta]_m(208\ nm)$ compared to $[\Theta]_m(222\ nm)$ and a shifting minimum from 208 nm to shorter wavelengths indicate random coil conformation.

An NPY analog having the structure Ac—RAAANLITRQRY—NH$_2$ was synthesized according to standard solid phase peptide synthetic techniques. The NPY analog was then dissolved in water at a concentration of 75 μM, and its CD measured using a JASCO J500 CD spectrometer at a temperature of both 3° C. and 25° C. Structure VI was synthesized according to Example 3, and its CD was similarly measured at both 3° C. and 25° C. (at a concentration of 75 μM). The results of this experiment are presented in Table 2.

TABLE 2

| Compound | Circular Dichroism | |
|---|---|---|
| | 222/208 3° C. | 222/208 25° C. |
| NPY Analog | 0.38 | 0.41 |
| Structure VI | 0.64 | 0.66 |

As illustrated by the data in Table 2, the alpha-helicity of the NPY analog was enhanced by the substitution of an alpha-helix mimetic of this invention within the peptide sequence. In particular, at 3° C. alphahelicity was increased from 0.38 to 0.64, and at 25° C. it was increased from 0.41 to 0.66. Since biological activity of the NPY analog has been correlated to alpha-helicity, the ability of the alpha-helix mimetics of this invention to enhance alpha-helicity will correspondingly enhance the biological activity of the NPY analog containing the alpha-helix mimetic.

From the foregoing, it will be appreciated that, although specific embodiments of this invention have been described herein for purposes of illustration, various modifications may be made without deviating from the spirit and scope of the invention. Accordingly, the invention is not limited except by the appended claims.

I claim:

1. An alpha-helix mimetic having the structure:

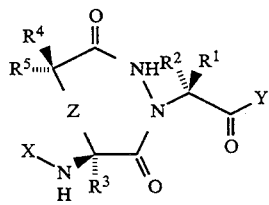

wherein Z is an optional methylene moiety; $R^1$ through $R^5$ are each selected from hydrogen and methyl; and X and Y are selected from the group consisting of amino acids, alpha-helix mimetics and terminating moieties.

2. The alpha-helix mimetic of claim 1 having the structure:

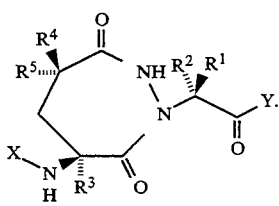

3. The alpha-helix mimetic of claim 1 having the structure:

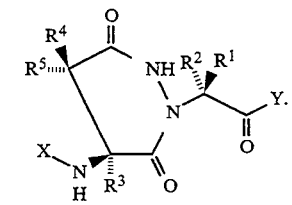

4. An alpha-helix mimetic having the structure:

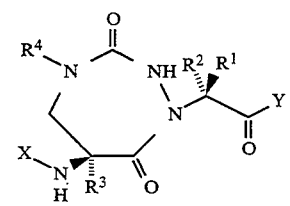

wherein $R^1$ through $R^4$ are each selected from hydrogen and methyl; and X and Y are selected from the group consisting of amino acids, alpha-helix mimetics and terminating moieties.

5. An alpha-helix modified peptide or protein, comprising a peptide or protein and an alpha-helix mimetic, the alpha-helix mimetic being covalently attached to at least one amino acid of the peptide or protein, wherein the alpha-helix mimetic has the structure:

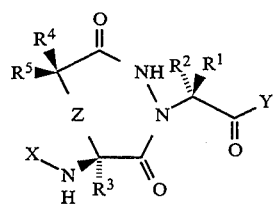

wherein Z is an optional methylene moiety; $R^1$ through $R^5$ are each selected from hydrogen and methyl; and at least X or Y is an amino acid of the peptide or protein.

6. The alpha-helix modified peptide or protein of claim 5 wherein both X and Y are amine acids of the peptide or protein.

7. An alpha-helix modified peptide or protein, comprising a peptide or protein and an alpha-helix mimetic, the alpha-helix mimetic being covalently attached to at least one amino acid of the peptide or protein, wherein the alpha-helix mimetic has the structure:

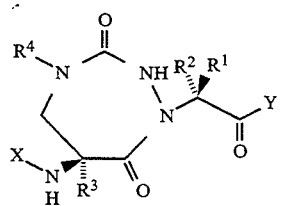

wherein $R^1$ through $R^4$ are each selected from hydrogen and methyl; and at least X or Y is an amino acid of the peptide or protein.

8. The alpha-helix modified peptide or protein of claim 7 wherein both X and Y are amino acid of the peptide or protein.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Arg  Ala  Ala  Ala  Asn  Leu  Ile  Thr  Arg  Gln  Arg  Tyr
1                  5                        10
```

(2) INFORMATION FOR SEQ ID NO:2:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:2:

```
Arg  Ala  Ala  Ala  Asn  Ala  Ala  Ala  Arg  Gln  Arg  Tyr
1                  5                        10
```

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:3:

```
Asn  Leu  Ile  Thr  Arg  Gln  Arg  Tyr
1                  5
```

(2) INFORMATION FOR SEQ ID NO:4:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:4:

```
Ala  Ala  Ala  Asn  Ala  Ala  Ala
1                  5
```

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:5:

```
Arg  Gln  Arg  Tyr
1
```

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:6:

```
Asn  Arg  Trp  Ile  Thr  Phe  Cys  Gln  Ser  Ile  Ile  Ser  Thr  Leu  Thr
1                  5                        10                       15
```

(2) INFORMATION FOR SEQ ID NO:7:

(i) SEQUENCE CHARACTERISTICS:

(A) LENGTH: 19 amino acids
(B) TYPE: amino acid
(D) TOPOLOGY: linear (ii) MOLECULE TYPE: peptide (xi) SEQUENCE DESCRIPTION: SEQ ID NO:7:

Asn Phe Leu Glu Arg Leu Lys Thr Ile Met Arg Glu Lys Tyr Ser Pro
1               5                   10                  15
Cys Ser Ser (2) INFORMATION FOR SEQ ID NO:8:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:8:

Ile Thr Phe Ala Gln Ser Leu Leu Ser Thr Leu Thr
1               5                   10

(2) INFORMATION FOR SEQ ID NO:9:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:9:

Gln Ser Leu Leu Ser Thr Leu Thr
1               5